(12) United States Patent
Renner et al.

(10) Patent No.: US 8,067,248 B2
(45) Date of Patent: Nov. 29, 2011

(54) METHOD FOR DIAGNOSING RHEUMATOID ARTHRITIS VIA ASSAYING MYOFIBROBLAST-LIKE SYNOVIOCYTES FOR FIBROBLAST ACTIVATION PROTEIN

(75) Inventors: Christopher Renner, Zurich (CH); Stëfän Bauer, Zurich (CH)

(73) Assignee: Luwig Institute for Cancer Research, New York, NY (US)

( * ) Notice: Subject to any disclaimer, the term of this patent is extended or adjusted under 35 U.S.C. 154(b) by 616 days.

(21) Appl. No.: 12/086,506

(22) PCT Filed: Dec. 5, 2006

(86) PCT No.: PCT/US2006/046608
§ 371 (c)(1),
(2), (4) Date: Nov. 4, 2008

(87) PCT Pub. No.: WO2007/111657
PCT Pub. Date: Oct. 4, 2007

(65) Prior Publication Data
US 2010/0266602 A1    Oct. 21, 2010

Related U.S. Application Data

(60) Provisional application No. 60/750,173, filed on Dec. 14, 2005.

(51) Int. Cl.
*G01N 33/53* (2006.01)
(52) U.S. Cl. ........... 436/811; 435/7.1; 435/7.92; 436/63
(58) Field of Classification Search ................... None
See application file for complete search history.

(56) References Cited

U.S. PATENT DOCUMENTS

| 5,587,299 | A | 12/1996 | Rettig et al. |
| 5,767,242 | A | 6/1998 | Zimmermann et al. |
| 6,455,677 | B1 | 9/2002 | Park et al. |
| 2002/0061839 | A1 | 5/2002 | Scharpe et al. |
| 2005/0272703 | A1 | 12/2005 | Wallner et al. |

OTHER PUBLICATIONS

Sedo et al., Dipeptidyl peptidase IV activity and/or structure homologs: Contributing factors in the pathogenesis of rheumatoid arthritis?, Arthritis Research & Therapy 2005, 7 pages 253-269.*
Garin-Chesa et al., "Cell surface glycoprotein of reactive stromal fibroblasts as a potential antibody target in human epithelial cancers," Proc. Natl. Acad. Sci. USA, vol. 87, pp. 7235-7239 (Sep. 1990).
Scanlan, et al., "Molecular cloning of fibroblast activation protein a, a member of the serine protease family selectively expressed in stromal fibroblasts of epithelial cancers," Proc. Natl. Acad. Sci. USA, vol. 91, pp. 5657-5661 (Jun. 1994).
Kelly, "Fibroblast activation protein-a and dipeptidyl peptidase IV (CD26): Cell-surface protease that activate cell signaling and are potential targets for cancer therapy," Drug Resistance Updates, vol. 8, pp. 51-58 (2005).

* cited by examiner

*Primary Examiner* — Melanie J Yu
*Assistant Examiner* — Gary W Counts
(74) *Attorney, Agent, or Firm* — Abelman, Frayne & Schwab

(57) ABSTRACT

The invention relates to methods for diagnosing rheumatoid arthritis by assaying for Fibroblast Activation Protein Alpha expression in rheumatoid, myofibroblast like synoviocytes. Therapeutic aspects are also a part of the invention.

8 Claims, No Drawings

SEQUENCE LISTING

<160> NUMBER OF SEQ ID NOS: 8

<210> SEQ ID NO 1
<211> LENGTH: 22
<212> TYPE: DNA

-continued

<213> ORGANISM: Homo sapiens

<400> SEQUENCE: 1
gttattgcct attcctatta tg                                            22

<210> SEQ ID NO 2
<211> LENGTH: 21
<212> TYPE: DNA
<213> ORGANISM: Homo sapiens

<400> SEQUENCE: 2
gtccatcatg aagggtggaa a                                             21

<210> SEQ ID NO 3
<211> LENGTH: 20
<212> TYPE: DNA
<213> ORGANISM: Homo sapiens

<400> SEQUENCE: 3
ctgaaggtga tgaagcagcc                                               20

<210> SEQ ID NO 4
<211> LENGTH: 20
<212> TYPE: DNA
<213> ORGANISM: Homo sapiens

<400> SEQUENCE: 4
agtccaagag aatggccgag                                               20

<210> SEQ ID NO 5
<211> LENGTH: 20
<212> TYPE: DNA
<213> ORGANISM: Homo sapiens

<400> SEQUENCE: 5
ctatggtcca ggagatgaag                                               20

<210> SEQ ID NO 6
<211> LENGTH: 20
<212> TYPE: DNA
<213> ORGANISM: Homo sapiens

<400> SEQUENCE: 6
agagtcttgc ctgtatcctc                                               20

<210> SEQ ID NO 7
<211> LENGTH: 23
<212> TYPE: DNA
<213> ORGANISM: Homo sapiens

<400> SEQUENCE: 7
cgtgagcgct tcgagatgtt ccg                                           23

<210> SEQ ID NO 8
<211> LENGTH: 23
<212> TYPE: DNA
<213> ORGANISM: Homo sapiens

<400> SEQUENCE: 8
cctaaccagc tgcccaactg tag                                           23

METHOD FOR DIAGNOSING RHEUMATOID ARTHRITIS VIA ASSAYING MYOFIBROBLAST-LIKE SYNOVIOCYTES FOR FIBROBLAST ACTIVATION PROTEIN

RELATED APPLICATION

This application claims priority of U.S. provisional application Ser. No. 60/750,173, filed on Dec. 14, 2005, the disclosure of which is incorporated by reference in its entirety.

FIELD OF THE INVENTION

This invention relates to certain molecules associated with rheumatoid arthritis cells. More particularly, it relates to fibroblast activation protein alpha ("FAP-α" hereafter) and its expression by rheumatoid myofibroblast-like synoviocytes. The molecule is a cell surface-bound type II transmembrane glycoprotein and has a molecular weight of from about 88 to about 95 kilodaltons as determined by SDS-PAGE. FAP-α has previously been identified as being associated with cancer cells and reactive with tumor stroma cells, but has not yet been identified as a marker for rheumatoid arthritis cells, i.e., synovial fibroblasts with a myofibroblastic phenotype. This, inter alia, is the subject of the invention. FAP-α is mainly expressed on the surface of mesenchymal cells that are involved in epithelium-mesenchyme interactions contributing to tissue remodeling. Nucleic acid molecules encoding FAP-α, portions thereof, FAP-α itself, and antibodies specific for FAP-α, such as monoclonal antibodies, or antibody fragments, are all useful in connection with features of the invention. All journal articles, cited to infra, are incorporated by reference in their entireties.

BACKGROUND AND PRIOR ART

FAP-α is a Mr 95 kDa cell surface-bound type II transmembrane glycoprotein and is a member of the serine prolyl oligopeptidase family. Comparison of amino acid sequences indicate that FAP-α is essentially identical to seprase (Goldstein L A, et al., *Biochim Biophys Acta* 1997, 1361(1):11-19) and is closely related to DPP IV (dipeptidylpeptidase IV), also known as CD26, another type II integral membrane protein. (Morimoto C, et al., *Immunol Rev* 1998, 161:55-70). These exoproteases cleave NH2-terminal dipeptides from polypeptides with L-proline or L-alanine immediately following the N-terminal amino acid. FAP-α has been found to have collagenase activity in vitro. (Goldstein L A, et al., supra; Jones B, et al., *Blood* 2003, 102(5):1641-1648). In addition to various families of proteolytic enzymes, such as matrix or disintegrin metalloproteases that serve as major collagenases, peptidase activity of FAP-α contributes to extracellular matrix ("ECM") degradation. (Park J E, et al., *J Biol Chem* 1999, 274(51):36505-36512; Ghersi G, et al., *J Biol Chem* 2002, 277(32):29211-29241). This is not only a fundamental property of normal tissue repair and remodeling, but is also involved in the pathological processes of invasive growth. This property correlates with the expression of FAP-α in granulation tissue of healing wounds (Grinnell F, *J Cell Biol* 1994, 124(4):401-404), desmoplastic reactions (Yen T W, et al., *Surgery* 2002, 131(2):129-134), and in more than 90% of human epithelial carcinomas. (Garin-Chesa P, et al., *Proc Nat'l Acad Sci USA* 1990, 87(18):7235-7239). FAP-α is mainly expressed on the surface of mesenchymal cells that are involved in epithelium-mesenchyme interactions contributing to tissue remodeling. Consistent with its mesenchymal origin, FAP-α is also occasionally expressed by bone and soft tissue sarcomas. (Rettig W J, et al., *Proc Natl Acad Sci USA* 1988, 85(9):31103114). Immunohistochemical staining of colorectal carcinomas and breast cancer (Park J E, et al., supra; Scanlan M J, et al., *Proc Natl Acad Sci USA* 1994, 91(12):5657-5661) confirmed the specific expression of FAP-α by tumor stroma fibroblasts but not by malignant cells themselves. (See also, Sappino A P, et al., *Int J Cancer* 1988, 41(5):707-712). Observations made during a clinical Phase I study, which examined the biodistribution of a humanized anti-FAP-α antibody in patients with advanced or metastatic PAP-a-positive cancer, a minor low-grade uptake in the knees and shoulders of three patients without clinical symptoms of arthritis, could have led to the conclusion that FAP-α might also be present in human joints. (Scott A M, et al., *Clin Cancer Res* 2003, 9(5):1639-1647). Unfortunately, no further explanation or discussion of this observation was presented. Further, it is unknown whether these patients were suffering from osteoarthritis. In contrast, resting fibrocytes in normal adult tissue generally lack detectable FAP-α expression. (Rettig W J, et al., supra; Garin-Chesa P, et al., *Proc Natl Acad Sci USA* 1990, 87(18):7235-7239).

Further information on FAP-α can be found in, e.g., U.S. Pat. Nos. 5,587,299; 5,767,242; 5,965,373; and 6,846,910, incorporated by reference in their entireties.

Rheumatoid arthritis ("RA") is a chronic inflammatory disease of unknown etiology and characterized by hyperplasia and chronic inflammation of the synovial membranes that invade deeply into the articular cartilage and bone. Activated fibroblast-like synoviocytes ("FLS") in the lining layer of the synovium are one of the dominant cells involved in pannus formation and are key players in joint destruction. (Firestein G S, *Arthritis Rheum* 1996, 39(11):1781-1790; Pap T, et al., *Arthritis Rheum* 2000, 43(11):2531-2536). Rheumatoid FLS have been shown to proliferate in an anchorage independent manner and express increased proliferation markers and matrix degrading enzymes when compared with FLS from patients with osteoarthritis ("OA"). (Qu Z, et al., *Arthritis Rheum* 1994, 37(2):212-220; Bucala R, et al., *J Exp Med* 1991, 173(3):569-574; Lafyatis R, et al., *J Clin Invest* 1989, 83(4):12671276). Expression of the CD44v7/8 epitope is linked to the proliferative behavior of FLS obtained from patients with RA, whereas expression of variants containing CD44v3 is linked with their increased invasive capacity (Croft D R, et al., *Eur J Immunol* 1997, 27(7):1680-1684; Wibulswas A, et al., *Am J Pathol* 2000, 157(6):2037-2044; Wibulswas A, et al., *Arthritis Rheum* 2002, 46(8):2059-2064). Matrix metalloproteases ("MMP") have been shown to be essential for degradation of the articular matrix, with MMP-1 and MMP-13 being considered as important candidates for joint destruction in RA (Tomita T, et al., *Arthritis Rheum* 2002, 46(2):373-378; Westhoff C S, et al., *Arthritis Rheum* 1999, 42(7):1517-1527). Invasion of migratory fibroblasts into connective tissue, however requires cell surface serine proteases, as well as metallocollagenases. (Ghersi G, et al., supra). Among these exoproteases that may cooperate with interstitial collagenase are groups of serine prolyl-peptidases such as DPP IV/CD26 and FAP-α/seprase. (Park J E, et al., supra; De Meester I, et al., *Immunol Today* 1999, 20(8):367-375). Fibroblasts with smooth muscle differentiation, termed myofibroblasts, are generally accepted to be the main source for extracellular matrix degrading factors. Furthermore, FLS with a myofibroblast-like molecular phenotype have been identified in the intimal lining layer of inflamed rheumatoid synovium. (Kasperkovitz P V, et al., *Arthritis Rheum* 2005, 52(2):430-441).

Despite the elucidation of FLS as a key player in joint inflammation and proteolytic enzymes like MMPs as representative markers for ECM degradation, no anti-fibroblast directed therapy is currently available. Approaches to inhibit the joint destructive process in RA by elimination or inhibition of one proteolytic enzyme did not produce sufficient results in clinical trials regardless of supportive in-vivo results. (Schedel J, et al., *Gene Ther* 2004, 11(13):1040-1047; Lewis E J, et al., *Br J Pharmacol* 1997, 121(3):540-546; Brown P D, *Expert Opin Investig Drugs* 2000, 9(9):2167-2177).

The difference between the targeting strategies of the approaches described supra, and a FAP-α-specific targeting approach, results from the substantial potential of FAP-α as a specific marker for synovial fibroblasts in RA, as described in the Detailed Description which follows. Thus, an embodiment of the present invention includes a diagnostic methodology for determining presence of RA in a patient, involving assaying a synovial tissue sample taken from the patient for the expression of FAP-α, wherein the expression of FAP-α is indicative of presence of RA in the patient.

Another embodiment of the present invention includes a therapeutic methodology involving inhibition of FAP-α playing its role in tissue remodeling, as well as focusing antibody mediated cytotoxic activity on this synovial cell type to eradicate FAP-α's role in the joint destructive process. It has now been found that these deleterious cells can be identified via analysis of at least one marker on their cellular surfaces. Identification of this marker has therapeutic ramifications which are set forth in the disclosure which follows.

These, as well as other features of the invention, will be disclosed in greater detail in the Detailed Description which follows.

DETAILED DESCRIPTION OF THE PREFERRED EMBODIMENTS

EXAMPLE I

This example describes experiments in which synovial tissue samples were collected from the diseased joints of patients. To elaborate, messenger RNA ("mRNA") was isolated from the collected synovial tissue samples, and reverse transcriptase polymerase chain reaction ("RT-PCR") was performed to amplify mRNA encoding specific proteins.

Synovial tissue was collected from a total of 20 patients during routine orthopedic surgery, i.e., ten patients with end-stage osteoarthritis ("OA"), and ten patients with refractory destructive rheumatoid arthritis ("RA") who underwent joint replacement surgery. The mRNA extraction and cDNA synthesis was performed immediately after surgery, and results obtained from these patients were compared to results obtained from control samples.

Specifically, synovial tissue was collected, using well known techniques which need not be elaborated here. A portion of the collected synovial tissue from each patient, as discussed supra, was homogenized immediately after surgery using a tissue tearer, and total RNA was extracted using commercially available products, and well established methods. The control samples included HT1080 cells transfected with FAP-α, mock-transfected cells (HT1080 par) (as described in Bauer S, et al., *J Immunol* 2004, 172(6):3930-3939), or cancer cells, taken from tumor samples from patients with breast cancer. The breast cancer cells were used as a positive control, because immunohistochemical staining of breast cancer confirmed the specific expression of FAP-α by tumor stroma fibroblasts but not by malignant cells themselves. (Park et al., *J Biol Chem* 1999, 274(51):36505-36512; Scanlan, et al., *Proc Natl Acad Sci USA* 1994, 91(12):5657-5661; and U.S. Pat. No. 5,587,299).

All samples were analyzed for mRNA transcripts coding for fragments of FAP-α (741 bp), MMP-1 (fibroblast type collagenase; collagenase-1; 428 bp) and MMP-1.3 (collagenase-3; 390 bp). The total amount of RNA present was quantified by spectrophotometry before first strand cDNA synthesis was performed, using commercially available products, and well established methods.

The following primers were used to generate specific cDNA-fragments (as described in Konttinen, et al., *Ann Rheum Dis* 1999, 58(11):691-697):

(a) the FAP-α PCR product was generated with

```
5'-GTTATTGCCTATTCCTATTATG-3'        (SEQ ID NO: 1)
and

5'-GTCCATCATGAAGGGTGGAAA-3';        (SEQ ID NO: 2)
```

(b) the MMP-1 PCR product was generated with

```
5'-CTGAAGGTGATGAAGCAGCC-3'         (SEQ ID NO: 3)
and

5'-AGTCCAAGAGAATGGCCGAG-3';        (SEQ ID NO: 4)
```

(c) the MMP-13 PCR product was generated with

```
5'-CTATGGTCCAGGAGATGAAG3'          (SEQ ID NO: 5)
and

5'-AGAGTCTTGCCTGTATCCTC-3';        (SEQ ID NO: 6)
```

(d) amplification of a genomic p53 fragment with the expected size Of 753 bp served as control, and the p53 PCR product was generated with

```
5'-CGTGAGCGCTTCGAGATGTTCCG-3'      (SEQ ID NO: 7)
and

5'-CCTAACCAGCTGCCCAACTGTAG-3'.     (SEQ ID NO: 8)
```

1 µl of any cDNA fragments produced were amplified with 1.25 unit of Taq DNA polymerase with 2.5 ml of 10× standard Taq buffer in a final volume of 25 µl containing 0.5 µl of nucleosidtriphosphate (10 mM), 0.5 of µl of each primer (10 µM), and distilled water.

PCR amplification was carried out using a thermocycler and the following cycling protocol: 95° C. for 5 mM, annealing for 60 seconds, and extension at 72° C. for 1 min. The number of cycles and the annealing temperature depended on the primers used: (a) FAP-α (55° C., 30 cycles); (b) MMP-1, (c) MMP-13 (62° C., 40 cycles); and (d) p53 (65° C., 25 cycles). Aliquots (20 µl) of each PCR product were separated on a 1.5% agarose gel and visualized by ethidium bromide staining.

The results showed that positive PCR controls were obtained from cDNA derived from FAP-α-transfected HT1080 cells or pooled breast cancer tumor samples (MMP-1 and MMP-13). Amplification of cDNA derived from mock transfected HT1080 cells was negative for the specific FAP-α fragments discussed above. Analysis of synovial tissue samples from patients with OA or RA demonstrate ubiquitous expression of all of collagenases-1 and -3 and FAP-α, but were found to be positive in RA samples to a much higher extent.

EXAMPLE II

This next example describes an experiment that was conducted to show differences in the translation of enzymes from mRNA, in synovial tissue samples from patients with OA as compared to patients with RA.

Immunohistochemical characterization of fibroblast populations (100-fold optical magnification) was performed. Collected synovial tissue samples, as discussed supra, were snap-frozen and sequential sections were stained for expression of a panel of activation markers including enzymes previously determined to be present by RT-PCR (e.g., Thy-1, FAP-α or SMA), in experiments not discussed herein.

To elaborate, the tissue samples referred to supra, were embedded in medium, snap-frozen in liquid nitrogen and then stored at −80° C. for immunohistochemical analysis. Sequential 5-μM sections were placed on microscope slides, and the slides were fixed in cold acetone (4° C. for 10 min), air dried, rehydrated in PBS and then blocked using a biotin blocking system.

Before adding a primary antibody (discussed infra), slides were blocked with rabbit serum using commercially available products, and well established methods. Following blocking, one of several different primary antibodies were added. These were murine F19 (mouse anti-human FAP-α mAb), anti-human CD90 (Thy-1; clone AS02), biotin-SP-conjugated rabbit anti-mouse IgG (irrelevant isotype matched IgG), 1:200, mouse anti-human CD44v3 (clone VFF-327), 1:50, mouse anti-human CD44v7/8 (clone VFF-17), 1:200, mouse anti-human smooth muscle actin (SMA; clone 1A4), 1:50, goat anti-human MMP-1 (C-18), goat anti human MMP-13 (D-17), and biotinylated rabbit anti-goat igG (irrelevant isotype matched IgG), 1:100. The murine F19, anti-human CD90 and biotin-SP-conjugated rabbit anti-mouse IgG were incubated for 60 minutes at room temperature, while the others were incubated at 4° C. overnight. A biotinylated secondary antibody (rabbit anti-mouse IgG, 1:500 or rabbit anti-goat IgG, 2 g/ml) and a preformed avidin-biotinylated horse radish peroxidase P-complex (ABC reagent) were used in accordance with standard protocols. The resulting antibody-ABC complex was visualized with a 3-amino 9 ethylcarbazole based chromogen (using commercially available products, and well established methods), resulting in pink-brown coloration of antigen-positive cells. All slides were counter-stained for about 5 min with Meyer's hematoxylin. Final slide adjustment was performed using commercially available products, and well established methods.

The results showed that the tissue samples from the OA and RA patients, as discussed supra, show distinct synovial fibroblast populations. Associated expression of SMA and FAP-α in the myofibroblasts of the intimal synovial lining is distinguished from Thy-1 positive fibroblasts, and from perivascular smooth muscle cells that only express SMA.

With respect to OA synovial fibroblasts, the results showed that these cells expressed CD90 (Thy-1) on their surface. The results also showed, however, a distinct OA synovial fibroblast population which completely lacked Thy-1 surface expression, but was clearly characterized by cell surface expression of FAP-α.

With respect to RA synovial fibroblasts, the results showed that the cell surface expression of FAP-α and SMA, i.e., the staining of anti-human FAP-α and anti-human SMA, was more intensive in this tissue as compared to the OA synovial fibroblasts, as discussed supra. Also, as shown in the OA synovial fibroblasts supra, the surface expression of FAP-α in the lining layer of the synovium is distinguished from non-proliferating and Thy-1 expressing fibroblasts of the structural scaffold.

EXAMPLE III

This example describes the visual scoring of the density of FAP-α-specific PCR-bands and of the intensity of histological FAP-α-detection, in the OA and RA synovial tissue samples, after RT-PCR analysis and immunohistochemistry was performed as described supra.

The visual scoring analysis was done by an independent observer, who was not made aware of the sample source being asserted. Comparison between synovial tissue samples taken from patients with OA and RA was performed using commercially available products, and well established methods. The scoring parameters were as follows: 1+: weak; 2+: modest; 3+: strong; 4+: very strong. P values <0.05 were considered statistically significant.

The results showed that the difference in density of PCR-bands, and intensity of histological FAP-α detection, between synovial tissue samples taken from patients with OA as compared to patients with RA, was significant ($p<0.0002$). The results are summarized in Table 1, which follows:

|  | Rheumatoid Arthritis | | | | | | | | | | Osteoarthritis | | | | | | | | | |
| --- | --- | --- | --- | --- | --- | --- | --- | --- | --- | --- | --- | --- | --- | --- | --- | --- | --- | --- | --- | --- |
| Patients | 01 | 02 | 03 | 04 | 05 | 06 | 07 | 08 | 09 | 10 | 01 | 02 | 03 | 04 | 05 | 06 | 07 | 08 | 09 | 10 |
| mRNA level | 3+ | 4+ | 3+ | 3+ | 3+ | 4+ | 2+ | 3+ | 2+ | 3+ | 2+ | 1+ | 2+ | 2+ | 1+ | 1+ | 2+ | 1+ | 1+ | 1+ |
| staining intensity | 3+ | 4+ | 2+ | 3+ | 3+ | 4+ | 2+ | 3+ | 2+ | 2+ | 1+ | 1+ | 2+ | 1+ | 1+ | 1+ | 1+ | 1+ | 1+ | 1+ |

In follow up, visual observation work, FAP-α positive FLS were analyzed to determine what activation molecules are associated with these cells. Using the same scoring system referred to, supra, SMA, CD44v33, CD44v7/8, MMP-1, MMP-13 expression levels were analyzed, in samples taken from 5 RA patients. The results are summarized in Table 2, which follows:

|  |  | FAP | SMA | CDRRv3 | CD4v7/8 | MMP-1 | MMP-13 |
| --- | --- | --- | --- | --- | --- | --- | --- |
| Patients | 01 | 3+ | 1+ | 1+ | 1+ | 1+ | 1+ |
|  | 02 | 4+ | 2+ | 1+ | 2+ | 1+ | 1+ |
|  | 03 | 3+ | 2+ | 1+ | 1+ | 1+ | 1+ |
|  | 04 | 3+ | 3+ | 1+ | 2+ | 1+ | 1+ |
|  | 05 | 3+ | 2+ | 1+ | 1+ | 1+ | 1+ |

EXAMPLE IV

The preceding examples demonstrate FAP-α expression in the synovial tissue samples studied. Further histomorphological analysis was carried out, using the methods and materials of example 2, supra, to further define the cell types in the samples analyzed. MMP-1, MMP-13, CD44v3, and CD44v7/8 were studied, as was SMA (400-fold optical magnification). The first four of these are known to be instrumental in ECM alteration in malignancies, and to be expressed in the synovial membranes of diseased joints, while SMA is a reliable means to identify the subpopulation of cells that are fibroblasts with myofibroblastic phenotype. This cell type is proteolytic.

Staining of perivascular smooth muscle cells showed that SMA was expressed by FAP-α positive, FLS cells, in the intimal lining area. This so-called "expression signature" is characteristic of FAP-α expressing myofibroblastic cells, which are the center of high inflammation activity in the rheumatoid synovium. This expression of FAP-α and SMA in synovial tissue samples of patients with RA was accompanied by accumulation of activation markers MMP-1 and MMP-13, and splice variants CD44v3 and CD44v7/8.

On the other hand, immunohistochemical analysis of the activation markers, referred to supra, in synovial tissue samples of patients with OA, showed limited staining for the MMPs and the CD44 variants. Specifically, the results showed only minor expression of MMP-1, MMP-13, and CD44v7/8 in areas that were slightly FAP-α positive.

There was a clear difference between OA and RA samples with respect to the expression pattern and staining intensity of the activation markers, referred to supra. Specifically, the RA samples showed a homogenous expression pattern and a homogenous staining intensity, which was not the case for the OA samples. The results also showed that the expression pattern and staining intensity of the RA tissue samples represented a stronger intensity of synovial inflammation when compared to the OA tissue samples.

Since FAP-α expression has been shown to be much more pronounced in RA tissue, as compared to OA tissue, this expression could be related to the degree of synovial inflammation (as discussed supra), as has already been demonstrated for MMPs and FAP-α in collagen induced arthritis ("CIA"). In mice, analysis of CIA gene expression profiles revealed a seven-fold increase in either FAP-α or MMP gene expression in inflamed when compared to non-inflamed paws. (McIndoe R A, et al., *Proc Natl Acad Sci USA* 1999, 96(5):2210-2214).

The fact that FLS in the rheumatoid synovium express FAP-α intensively, permits the artisan to screen for therapeutic agents, such as, but not being limited to, enzymatic substrates. The probability of enzymatic activity is supported by immunohistochemistry, as described supra. As shown by the results described herein, characterization of the synovial lining layer in RA patients revealed that FAP-α expression is accompanied by accumulation of other degradation markers that are predominantly found in this area, e.g., MMP-1, MMP-13 as well as CD44v3 and CD44v7/8. These markers are instrumental in extracellular matrix remodeling in malignancies and are also already known to be present in the synovial membranes of diseased joints (Croft DR, et al., supra; Wibulswas A, et al., *Am J Pathol* 2000, 157(6):2037-2044; Wibulswas A, et al., *Arthritis Rheum* 2002, 46(8):2059-2064); Tomita T, et al., supra; Westhoff C S, et al., *Arthritis Rheum* 1999, 42(7):1517-1527). In addition, fibroblasts of the myofibroblastic phenotype were shown to be the major cell type expressing FAP-α in RA patients, as discussed supra. These fibroblasts are also the major source of other proteolytic enzymes and are generally thought to be responsible for ECM degradation. (Kasperkovitz PV, et al., supra; Sundarrajan M, et al.; *Arthritis Rheum* 2003, 48(9):2450-2460; Yamamoto N, et al., *Clin Invest* 2003, 112(2):181-188).

As discussed supra, a reliable marker to identify fibroblasts of the myofibroblastic phenotype is SMA, and immunohistochemistry revealed the expression of SMA by FAP-α-positive FLS in the intimal lining layer of the rheumatoid synovium. This expression signature characterizes the area of FAP-α-expressing myofibroblastic cells as the centre of high-inflammation activity in the rheumatoid synovium and discriminates from Thy-1 positive non-proliferating fibroblasts in the synovial matrix. (Seemayer C A, et al., *Am J Pathol* 2003, 162(5):1549-1557).

The value of FAP-α as a therapeutic target in RA and OA is twofold: First, since the proteolytic activity of FAP-α contributes to ECM degradation, inhibition thereof is an attractive goal. In this context, it needs to be noted that suppression of FAP-α's enzymatic activity by PT-100 (which is a modified dipeptide, i.e., the boronic dipeptide Val-boro-Pro) resulted in potent antitumor effects and augmented antibody-dependent cell-mediated cytotoxicity in murine tumor models. (Adams S, et al., *Cancer Res* 2004, 64(15):5471-5480; Cheng JD, et al., *Mol Cancer Ther* 2005, 4(3):351-360) (The structure of PT-100 is provided in FIG. 1 of Adams). Second, FAP-α has now been shown to be a marker for the identification of the subset of FLS cells with the highest proteolytic activity. The genetically stable and restricted expression of FAP-α (Garin-Chesa P, et al., supra) has lead to the establishment of several preclinical strategies for tumor therapy. (Bauer S, et al., supra; Cheng JD, et al., *Cancer Res* 2002, 62(16):4767-4772; Samel D, et al., *J Biol Chem* 2003, 278 (34):32077-32082). The use of anti-FAP-α antibody-based cancer immunotargeting has even been proven in a clinical Phase I dose-escalation study (Scott A M, et al., supra).

Therefore, since FAP-α has been shown to be a valuable therapeutic marker in cancer, e.g., antitumor effects, and FAP-α appears to be a valuable marker for the identification of FLS, it is seen that different pathological conditions, such as rheumatoid arthritis, which are characterized by abnormal expression of FAP-α, are amenable to treatment with anti-FAP-α agents, such as antagonists, including peptides, modified peptides, and so forth.

Other aspects of the invention will be clear to the skilled artisan, and need not be set forth here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

The invention claimed is:

1. A method of determining presence of rheumatoid arthritis ("RA") in a patient, comprising taking a sample of synovial tissue from said patient, assaying said sample of synovial tissue taken from said patient for expression of FAP-α, wherein expression of said FAP-α in the sample of synovial tissue taken from said patient is indicative of RA in said patient.

2. The method of claim 1, further comprising amplifying a nucleic acid molecule which encodes FAP-α as an indication of RA.

3. The method of claim 1, wherein said amplifying comprises polymerase chain reaction.

4. The method of claim 1, further comprising assaying said sample for a protein expressed by a nucleic acid molecule which encodes FAP-α.

5. The method of claim 4, wherein said assay is an immunoassay.

6. The method of claim 5, wherein said assay is an immunohistochemical assay.

7. The method of claim 4, wherein said immunoassay comprises contacting said sample with a monoclonal antibody which binds specifically for FAP-α.

8. The method of claim 7, wherein said monoclonal antibody is a mouse anti-human antibody.

* * * * *